United States Patent [19]

Coker et al.

[11] Patent Number: 4,590,199
[45] Date of Patent: May 20, 1986

[54] ANTIHISTAMINIC 2-(AMINO ETHYLAMINO) PYRIDINES

[76] Inventors: Geoffrey G. Coker, 80 Pickhurst Park, Bromley, Kent, England; John W. A. Findlay, Rte. 2, Box 514, Cascade Dr., Chapel Hill, N.C.

[21] Appl. No.: 635,308

[22] Filed: Jul. 27, 1984

[30] Foreign Application Priority Data

Aug. 1, 1983 [GB] United Kingdom ............... 8320699

[51] Int. Cl.$^4$ .................. A61K 31/455; A61K 31/44; C07D 401/12; C07D 213/80
[52] U.S. Cl. .................... 514/343; 514/352; 546/281; 546/309; 546/310; 546/312
[58] Field of Search ............... 546/310, 312, 309, 281; 514/343, 352

[56] References Cited

U.S. PATENT DOCUMENTS 2,502,151  8/1946  Horclois ..................... 546/329
3,415,834 12/1968  Hoffmann et al. .............. 260/295.5
4,501,893  2/1985  Findlay et al. ............... 546/281

FOREIGN PATENT DOCUMENTS 1445677 12/1968  Fed. Rep. of Germany .
2106902  4/1983  United Kingdom ............ 546/312

OTHER PUBLICATIONS

European Search Report of EP 84109056.6.

Primary Examiner—Henry R. Jiles
Assistant Examiner—Dale A. Bjorkman
Attorney, Agent, or Firm—Donald Brown

[57] ABSTRACT

The present invention provides a compound of the formula (I):

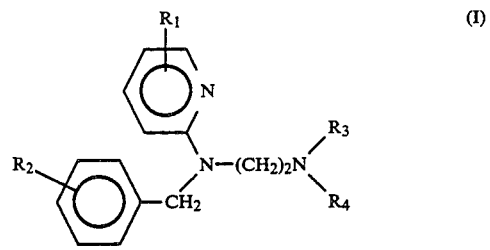

or a salt, ester or amide thereof; wherein $R_1$ is —COOH, —CH=CH—COOH, —CH$_2$COOH, or (CH$_2$)$_2$COOH. $R_2$ is alkoxy (1–4 carbons), alkyl (1–4 carbons), hydrogen, or halogen. $R_3$ and $R_4$ may be the same or different and can be hydrogen, or lower alkyl(1–4 carbons) or $NR_3R_4$ is pyrrolidino.

Also disclosed are methods for the preparation of the above compounds and pharmaceutical formulations containing them.

The above compounds have antihistaminic activity.

15 Claims, No Drawings

ANTIHISTAMINIC 2-(AMINO ETHYLAMINO) PYRIDINES

The present invention relates to new chemical compounds exhibiting antihistamine activity with low sedative potential.

U.S. Pat. No. 2,502,151 discloses a group of substituted ethylenediamines with one terminal nitrogen bearing two methyl groups and the other nitrogen bearing a substituted benzyl and a heteroaromatic group with antihistamine activity, the most outstanding of which is the compound named N,N-dimethyl-N'-(4-methoxyphenylmethyl)-N'-2-pyridyl-1,2-ethanediamine and hereinafter referred to by its generic name, pyrilamine. Pyrilamine has gained a fair degree of clinical acceptance; however, like all other potent antihistamines in clinical use at the present it produces sedation and drowsiness in varying degrees in most patients (L. Goodman and A. Gilman, *The Pharmacological Basis of Therapeutics*, 4th ed., p. 640, Macmillan, New York, 1970). This sedating effect limits the use of antihistamines by patients who must operate machinery, drive motor vehicles or must engage in activities requiring mental alertness.

The antihistamines now in use, eg. diphenhydramine, pheniramines, pyrilamine, promethazine and triprolidine, exhibit varying degrees of anticholinergic activity. Such activity causes dryness of mouth, blurred vision and tachycardia and is generally regarded as undesirable.

A novel group of compounds having potent antihistamine activity which are substantially free from sedative effects, and which will have little or no anticholinergic effect has now been discovered.

Accordingly this invention provides the compounds of formula (I).

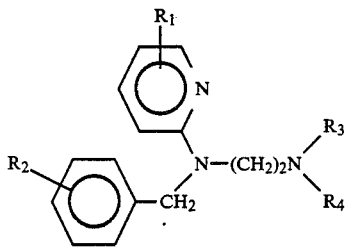

wherein $R_1$ is —COOH, —CH=CH—COOH, —CH$_2$COOH, or (CH$_2$)$_2$ COOH. $R_2$ is alkoxy (1–4 carbons), alkyl (1–4 carbons), hydrogen, or halogen. $R_3$ and $R_4$ may be the same or different and can be hydrogen, or lower alkyl (1–4 carbons) or NR$_3$R$_4$ is pyrrolidino.

This invention also includes ester and amide derivatives as well as acid addition salts and salts of the carboxylic acid group of the compounds of formula (I).

Of the compounds of formula (I) (E)-3-(6-dimethylaminoethyl)-4-methoxy-benzylamino)-2-pyridyl)acrylic acid (Compound A) and 6-(N-(2-dimethylaminoethyl)-4-methoxybenzylamino) nicotinic acid (Compound B) were found to be particularly active.

Compounds of formula (I) and their salts may be synthesized by methods known in the art for the synthesis of compounds having analogous structures.

1. A method for preparing compounds of formula (I) when $R_1$ is —CH=CH—COOH comprises reacting a compound of formula (II) with a compound of formula (III) by the Wittig method (see *Organic Reactions*, 14, 270–490 (1965) and *Pure and Applied Chemistry*, 9, 245–254 (1964)).

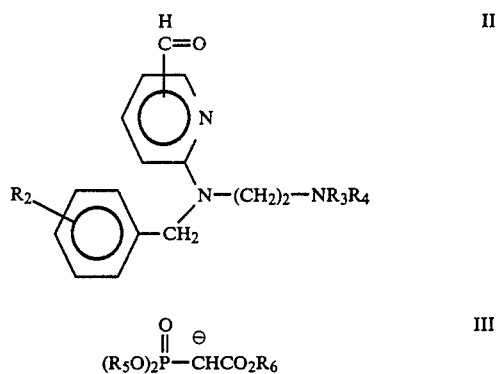

wherein $R_2$, $R_3$ and $R_4$ are as defined above $R_5$ is lower alkyl or phenyl and $R_6$ is lower alkyl.

An alternate synthesis of compounds of formula (I) where $R_1$ is —CH=CH—COOH comprises reacting a compound of formula (II) with malonic acid via the well known Knoevenagel reaction (H. O. House, *Modern Synthetic Reaction*, W. A. Benjamin, California, 1972).

Compounds of formula (II) may be prepared by reacting the corresponding compound of formula (IV) with n-butyllithium

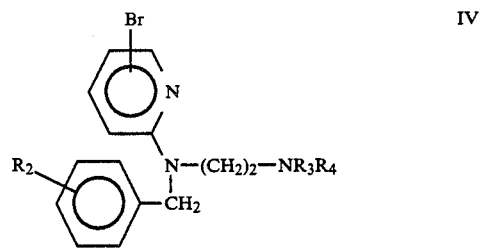

followed by treatment with dimethylformamide. In turn compounds of formula IV may be prepared by reacting 2,6-dibromopyridine with the corresponding compound of formula (V).

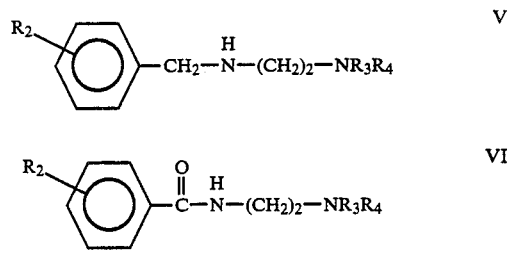

Compounds of formula (V) may be prepared by reduction of compounds of formula (VI) with reagents such as lithium aluminum hydride. The compounds formula (VI) in turn may be synthesized by reacting compounds of formula (VII) with the substituted ethylenediamines of formula (VIII).

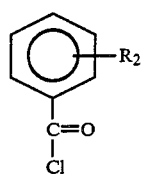

VII

H₂N(CH₂)₂NR₃R₄            VIII

Compounds of formula (V) may also be prepared by reductive amination (for example with sodium cyanoborohydride in methanol) of the appropriate benzaldehyde with an ethylenediamine of formula (VIII).

2. A method for preparing compounds of formula I when $R_1$ is —COOH comprises reacting the corresponding compound of formula IV with n-butyllithium followed by treatment with $CO_2$, or by oxidation of the aldehyde (II) with silver oxide.

3. The compounds of formula (I) when $R_1$ is —$(CH_2)_2CO_2H$ can be produced by reduction, e.g. by catalytic hydrogenation with platinum of the corresponding acrylic acid derivative described hereinabove in method 1.

4. The compounds of formula (I) where $R_1$ is —$CH_2COOH$ can be prepared by reacting the aldehydes of formula (II) with Wittig reagents or equivalents of the compounds of formula (IX) to give compounds of formula (X) which are converted to compounds of formula (I) by acid hydrolysis.

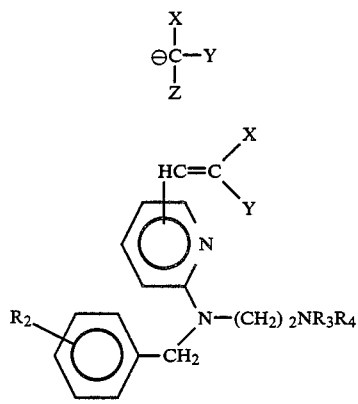

| WHERE | | |
| X | Y | Z |
| SOCH₃ | SCH₃ | H |
| PO(OC₂H₅)₂ | N(CH₃)₂ | H |
| —S(CH₂)₃*S— | | P(OCH₃)₃ |
| —S(CH₂)₃*S— | | Si(CH₃)₃ |

*X AND Y TAKEN TOGETHER

Compounds of this invention have the same utilities as antihistamines used clinically at present. They may be used to relieve symptoms of nasal stuffiness due to colds and vasomotor rhinitis and for the symptomatic control of all allergic conditions including nasal allergy, perennial rhinitis, urticaria, angioneurotic oedema, allergic conjunctivitis, food allergy, drug and serum reactions, insect bites and stings and desensitizing reactions. The compounds are also indicated in all conditions responsive to its antipruritic activity including allergic dermatoses, neurodermatitis, anogenital pruritus, and pruritus of non-specific origin such as eczema, and of specific cause such as chickenpox, photosensitivity and sunburn. In contrast to the antihistamines in present use, the compounds of this invention are not sedating and have little or no anticholinergic side effects.

The amount of active compound required for use in the above conditions will vary both with the route of administration, the condition under treatment and the mammal undergoing treatment, and is ultimately at the discretion of the physician. A suitable oral dose of the active compound for a mammal is in the range of from 0.3 to 6.0 mg per kilogram body weight per day; preferably from 0.9 to 3.0 mg/kg. For example a typical dose for a human recipient of compound (A) is 2.1 mg/kg body weight per day.

The desired daily dose is preferably presented as from one to six sub-doses administered at appropriate intervals throughout the day as needed. Where three sub-doses of compounds of formula (I) are employed, each will preferably lie in the range of from 0.3 to 1.0 mg/kg body weight; for example, a typical sub-dose of compund for a human recipient is about 50 mg.

While it is possible for the active compound previously described to be administered alone as the raw chemical, it is preferable to present the active compound, a compound of formula (I), as a pharmaceutical formulation. Formulations of the present invention, both for veterinary and for human medical use, comprise the active compound together with one or more pharmaceutically acceptable carriers thereof and optionally any other therapeutic ingredients. For example, the active compound may be formulated with a sympathomimetic agent such as the decongestant pseudoephedrine, an antitussive such as codeine, an analgesic, an antiinflammatory, an antipyretic, or an expectorant. The carrier(s) must be pharmaceutically acceptable in the sense of being compatible with the other ingredients of the formulation and not deleterious to the recipient thereof.

The formulations include those suitable for oral, rectal, topical, nasal, ophthalmic or parenteral (including subcutaneous, intramuscular and intravenous) administration.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier or both and then, if necessary, shaping the product into the desired formulations.

Formulations of the present invention suitable for oral administration may be presented as discrete units such as capsules, cachets, tablets or lozenges, each containing a predetermined amount of the active compound (defined herein as a compound of formula (I)); as a powder or granules; or a suspension in an aqueous liquid or non-aqueous liquid such as a syrup, an elixir, an emulsion or a draught.

A tablet may be made by compression or molding, optionally with one or more accessory ingredients. Compressed tablets may be prepared by compressing in a suitable machine, with the active compound being in a free-flowing form such as a powder or granules which is optionally mixed with a binder, disintegrant, lubricant, inert diluent, surface active agent or dispersing agent. Molded tablets comprised of a mixture of the powdered active compound with any suitable carrier may be made by molding in a suitable machine.

A syrup may be made by adding the active compound to a concentrated, aqueous solution of a sugar for example sucrose to which may also be added any accessory ingredient(s). Such accessory ingredient(s) may include flavourings, an agent to retard crystallization of the sugar or an agent to increase the solubility of any other ingredient, such as a polyhydric alcohol for example, glycerol or sorbitol, and suitable preservatives.

Formulations for rectal administration may be presented as a suppository with a usual carrier such as cocoa butter, or hydrogenated fats or hydrogenated fatty carboxylic acids.

Formulations suitable for parenteral administration conveniently comprise a sterile aqueous preparation of the active compound which is preferably isotonic with the blood of the recipient.

Nasal spray formulations comprise purified aqueous solutions of the active compound with preservative agents and isotonic agents. Such formulations are adjusted to a pH and isotonic state compatible with the nasal mucous membranes.

Ophthalmic formulations are prepared by a similar method to the nasal spray except the pH and isotonic factors are adjusted to match that of the eye.

Topical formulations comprise the active compound dissolved or suspended in media such as mineral oil, petrolatum, polyhydroxy alcohols or other bases used for topical pharmaceutical formulations. The addition of other accessory ingredients, vide infra, may be desirable.

In addition to the aforementioned ingredients, the formulations of this invention may further include one or more accessory ingredient(s) selected from diluents, buffers, flavouring agents, binders, disintegrants, surface active agents, thickeners, lubricants, preservatives (including antioxidants) and the like.

When used in medicine, the salts of the compound of formula (I) should be both pharmacologically and pharmaceutically acceptable, but non pharmaceutically acceptable salts may conveniently be used to prepare the free active compound or pharmaceutically acceptable salts thereof and are not excluded from the scope of this invention. Such pharmacologically and pharmaceutically acceptable salts include, but are not limited to, those prepared from the following acids: hydrochloric, hydrobromic, sulphuric, nitric, phosphoric, maleic, salicylic, toluene-p-sulphonic, tartaric, citric, methanesulphonic, formic, malonic, succinic, naphthalene-2-sulphonic and benzenesulphonic. Also pharmaceutically acceptable salts can be prepared as alkaline metal or alkaline earth salts, such as sodium, potassium or calcium salts of the carboxylic acid group.

The following examples are provided by the way of illustration of the present invention and should in no way be construed as a limitation thereof. All temperatures indicated are in degrees Celsius.

EXAMPLE 1

(E-3-(6-N-(2-Dimethylaminoethyl)-4-methoxybenzylamino)-2-pyridyl)acrylic acid

A solution of unsym-N,N-dimethylethylenediamine (100 g, 1.13 mole) in 500 mL of tetrahydrofuran and 500 mL of 2M sodium hydroxide was cooled in an ice bath and p-anisoyl chloride (99 g, 0.58 mole) was added dropwise with stirring. The reaction was allowed to warm to room temperature and was stirred overnight. The solution was extracted with four 300 mL portions of ether which were dried over magnesium sulfate, and the solvent was removed in vacuo to give 107 g (83%) of N-(2-dimethylaminoethyl)-4-methoxybenzamide as a pale yellow liquid which crystallized on standing. A portion was recrystallized from ether to give a white crystalline solid, m.p. 53°-54°. Calc. for $C_{12}H_{18}N_2O_2$: C, 64.84; H, 8.16; N, 12.60. Found: C, 64.82; H, 8.19; N, 12.57.

The amide from above (103.5 g, 0.466 mole) was dissolved in 1000 mL of dry tetrahydrofuran under nitrogen and added dropwise to 18 g (0.47 mole) of lithium aluminum hydride at 0°. The reaction was heated at reflux for 16 hrs, then cooled to room temperature. A saturated aqueous solution of sodium sulfate (35 mL) was added dropwise over 1 hr and the solution was filtered, rinsing the granular precipitate with methylene chloride. The filtrate was dried over sodium sulfate and the solvent removed in vacuo to give 86 g of liquid which was a 3:1 mixture of the desired product and starting material. The reduction procedure above was repeated on the mixture with 23 g of lithium aluminum hydride to give 65 g of N,N-dimethyl-N'-(4-methoxybenzyl)-1,2-ethanediamine as a pale yellow liquid.

The diamine from above (30.6 g, 0.147 mole) was dissolved in 120 mL of dry pyridine with 35 g (0.147 mole) of 2,6-dibromopyridine and heated at reflux under nitrogen for 18 hrs. The pyridine was removed in vacuo and the residue was redissolved in 700 mL of methylene chloride, washed with 300 mL of 1M sodium hydroxide, dried over sodium sulfate, and the solvent evaporated to give 61 g of black oil. The product was purified by silica gel chromatography on the Waters Prep 500 instrument (methylene chloride containing 0.1% of ethanol and 0.1% of triethylamine) to give 8.2 g of N-(6-bromo-2-pyridyl)-N-(4-methoxybenzyl)-N',N'-dimethyl-1,2-ethanediamine as a brown oil. The hydrochloride salt was prepared by dissolving the oil in methylene chloride and shaking with 1M hydrochloric acid which was 2-3M in sodium chloride. The methylene chloride solution was dried over magnesium sulfate and the solvent removed to give 8.20 g (13%) of the hydrochloride salt as a brown foam. Crystallization of a portion from isopropanol and ether gave beige crystals, m.p. 102°-106°. Calc. for $C_{17}H_{22}BrN_3O.HCl.0.5\ H_2O$: C, 49.83; H, 5.90; N, 10.25. Found: C, 49.81; H, 5.93; N, 10.23.

The free base of the above bromopyridine derivative (7.00 g, 19.2 mmol) was dissolved in 100 mL of anhydrous tetrahydrofuran under nitrogen and dried over 4A molecular sieves for 24 hrs. The solution was transferred to a dry flask under nitrogen and cooled to −78°, then 13 mL of 1.5M n-butyllithium in hexane (19.5 mmol) was added dropwise. The reaction was allowed to warm to −10°, then was cooled again to −78° and 1.6 mL (20.6 mmol) of dimethylformamide was added. After warming to 0°, the reaction was poured into 75 mL of 1M hydrochloric acid and extracted with 150 mL of ether. The ethereal extract was back-extracted with three 50 mL portions of water. Combined aqueous and acid solutions were basified with 1M sodium hydroxide and extracted with four 100 mL portions of ether which were dried over sodium sulfate and evaporated to give 5.65 g of dark oil. Silica gel chromatography (Waters Prep 500, methylene chloride containing 1% ethanol and 0.1% triethylamine) provided 2.25 g (38%) of 6-(N-

(2-dimethylaminoethyl)-4-methoxybenzylamino)-picolinaldehyde.

Triethylphosphonoacetate (0.88 mL, 4.4 mmol) in 10 mL of benzene was added dropwise to 200 mg of 50% sodium hydride dispersion in 10 mL of benzene and stirred at room temperature until gas evolution ceased. A solution of the aldehyde from above (1.18 g, 3.77 mmol) in 10 mL of methylene chloride was added to the reaction and allowed to stir overnight at room temperature. Aqueous 1M sodium hydroxide (20 mL) was added to the reaction and the mixture was extracted with three 25 mL portions of chloroform which were dried over sodium sulfate and evaporated to give 1.36 g of crude product. Chromatography on silica gel (Waters Prep 500, methylene chloride containing 0.5% ethanol and 0.1% triethylamine) gave 297 mg (20%) of (E)-ethyl 3-(6-(N-(2-dimethylaminoethyl)-4-methoxybenzylamino)-2-pyridyl)acrylate as a yellow gum.

The ester from above (297 mg, 0.77 mmol) was dissolved in 10 mL of methanol with 4 mL of 1M potassium hydroxide and stirred overnight at room temperature. The solvent was removed under vacuum and the residue was redissolved in 20 mL of water and extracted with two 20 mL portions of ether. The aqueous layer was adjusted to a pH of 7 with 1M hydrochloric acid and the powdery precipitate was collected by filtration to give 165 mg of (E)-3-(6-(N-(2-dimethylaminoethyl)-4-methoxybenzylamino)-2-pyridyl)acrylic acid as the dihydrate, mp. 75°–81°. Calc. for $C_{20}H_{25}N_3O_3.2H_2O$: C, 61.36; H, 7.47; N, 10.73. Found: C, 61.26; H, 7.44; N, 10.67.

EXAMPLE 2

6-(N-(2-Dimethylaminoethyl)-4-methoxybenzylamino)-nicotinic acid

N-(5-Bromo-2-pyridyl)-N-(4-methoxybenzyl)-N',N'-dimethyl-1,2-ethanediamine (D. H. Marrian, S. J. Hill, J. K. M. Sanders, and J. M. Young, *J. Pharm. Pharmac.*, 30, 660 (1978)) (4.26 g, 11.7 mmol) in 35 mL of tetrahydrofuran was cooled to −78° under nitrogen atmosphere and 7.6 mL (11.7 mmol) of 1.55M n-butyllithium in hexane was added dropwise. The dark brown solution was stirred at −78° for five minutes, then carbon dioxide gas was bubbled into the reaction until the color changed to bright yellow. The reaction was warmed to room temperature and the solvent was evaporated in vacuo. The residue was dissolved in 100 mL of water and the pH was adjusted to 11 with 1M sodium hydroxide. The solution was extracted with 75 mL of chloroform and then the chloroform was back-extracted with two 50 mL portions of 0.1M sodium hydroxide. The combined water layers were warmed briefly under aspirator vacuum to remove suspended chloroform, then the pH was adjusted to 8 with 1M hydrochloric acid. After cooling in an ice bath for one hour, filtration gave 2.20 g (56%) of 6-(N-(2-dimethylaminoethyl)-4-methoxybenzylamino)nicotinic acid as a white powder, mp. 188°–190°. Calc. for $C_{18}H_{23}N_3O_3.0.25 H_2O$: C, 64.75; H, 7.09; N, 12.58. Found: C, 64.80; H, 7.09; N, 12.59.

EXAMPLE 3

Antihistaminic Activity

In vitro antihistaminic activity: The longitudinal muscle was isolated from the intact ileum of guinea-pigs (Hartley, male 250–400 g) and placed in an organ bath under 300 mg tension. After one hour of equilibration, cumulative concentration-response curves (Van Rossum, J. M., *Arch. Int. Pharmacodyn. Ther.* 143, 299–330, 1963) to histamine were obtained. Following washing, the tissues were incubated for one hour with the test compound and then a second histamine concentration-response curve was run. Shifts to the right of the agonist concentration-response curve produced by the antagonists were used to construct Schild plots (Arunlakshana, O. and Schild, H. O., *Br. J. Pharmacol.* 14, 48–58, 1959). Regression of Log (dr-1) on Log [B], where dr is an equiactive response in the presence and absence of antagonist and [B] is the molar concentration of antagonist, allowed an estimate of $pA_2$, i.e. the negative log of the concentration of antagonist which shifts the control histamine concentration-response curve 2X to the right.

TABLE I

| Results of Antihistamine Assays | |
|---|---|
| Compound | $pA_2$ |
| Pyrilamine | 9.4* |
| A | 6.6 |
| B | 5.9 |

*R.B. Barlow, Introduction to Chemical Pharmacology, 2nd ed., p. 357, Wiley, New York, 1964.

EXAMPLE 4

Formulations

| (A)-Injection | |
|---|---|
| Ingredient | Amount per ampoule |
| Compound of formula (I) | 50.0 mg |
| Water for Injections, q.s. | 1.0 mL |

The finely ground active compound was dissolved in the water for Injections. The solution was filtered and sterilized by autoclaving.

| (B)-Suppository | |
|---|---|
| Ingredient | Amount per suppository |
| Compound of Formula (I) | 50.0 mg |
| Cocoa Butter, or Wecobee ™ Base q.s. | 2.0 g |

Wecobee is a trademark and is a hydrogenated fatty carboxylic acid.

The finely ground active compound was mixed with the melted suppository base (either Cocoa Butter or Wecobee ™ base), poured into molds and allowed to cool to afford the desired suppositories.

| (C)-Syrup | |
|---|---|
| Ingredient | Amount per 5 mL |
| Compound of Formula (I) | 50.0 mg |
| Ethanol | 0.3 mg |
| Sucrose | 2.0 mg |
| Methylparaben | 0.5 mg |
| Sodium Benzoate | 0.5 mg |
| Cherry Flavour | q.s. |
| Coloring | q.s. |
| Water q.s. to | 5.0 mL |

Ethanol, sucrose, sodium benzoate, methylparaben, and flavouring were combined in 70% of the total batch quantity of water. Coloring and the active compound were dissolved in the remaining water, then the two solutions were mixed and clarified by filtration.

| (D)-Tablet | |
| --- | --- |
| Ingredient | Amount per Tablet |
| Compound of Formula (I) | 50.0 mg |
| Lactose | 60.0 mg |
| Corn Starch, Pregelatinized | 2.5 mg |
| Potato Starch | 12.0 mg |
| Magnesium stearate | 0.5 mg |

The active compound was finely ground and intimately mixed with the powdered excipients lactose, corn starch, potato starch and magnesium stearate. The formulation was then compressed to afford a tablet weighing 125 mg.

| (E)-Capsule | |
| --- | --- |
| Ingredient | Amount per Capsule |
| Compound of Formula (I) | 50.0 mg |
| Lactose | 440.0 mg |
| Magnesium Stearate | 5.0 |

The finely ground active compound was mixed with the powdered excipients lactose, corn starch and stearic acid and packed into gelatin capsules.

| (F)-Tablet | |
| --- | --- |
| Ingredient | Amount per Tablet |
| Compound of Formula (I) | 50.0 mg |
| Pseudoephedrine HCl | 60.0 mg |
| Lactose | 62.5 mg |
| Potato Starch | 14.0 mg |
| Magnesium Stearate | 1.0 mg |
| Gelatin | 2.8 mg |

A tablet was prepared from the above formulation by the method previously described in Example 7(D).

| (G)-Syrup | |
| --- | --- |
| Ingredient | Amount per 5 mL |
| Compound of Formula (I) | 50.0 mg |
| Pseudoephedrine HCl | 30.0 mg |
| Codeine Phosphate | 10.0 mg |
| Guaifenesin | 100 mg |
| Methylparaben | 0.5 mg |
| Sodium benzoate | 0.5 mg |
| Flavor | q.s. |
| Color | q.s. |
| Glycerol | 500 mg |
| Sucrose | 2000 mg |
| Purified Water q.s. to | 5.0 mL |

A syrup containing other active ingredients in addition to a compound of formula (I) was prepared from the above ingredients by an analogous method to that described for Example 7(C) above.

| (H)-Nasal Spray | |
| --- | --- |
| Ingredient | Amount per 100.0 mL |
| Compound of Formula (I) | 5 g |
| Sodium Chloride | 0.8 g |
| Preservative | 0.5 g |
| Purified Water q.s. | 100.0 mL |

The preservative was dissolved in warm purified water and after cooling to 25°–30° C. the sodium chloride and the compound of formula (I) were added. The pH was then adjusted to 5.5–6.5 and purified water was added to bring the final volume to 100.0 mL.

| (I)-Ophthalmic Solution | |
| --- | --- |
| Ingredient | Amount per 100.0 mL |
| Compound of Formula (I) | 1.0 g |
| Sodium Chloride | 0.8 g |
| Preservative | 0.5 g |
| Water for Injection q.s. | 100.0 mL |

This formulation was prepared in a similar way to the nasal spray.

| (J)-Topical Cream | |
| --- | --- |
| Ingredient | Amount per 100.0 mL |
| Compound of Formula (I) | 5.0 g |
| Emulsifying Wax, N.F. | 15.0 g |
| Mineral Oil | 5.0 g |
| White Petrolatum | 5.0 g |
| Preservative | 0.25 g |
| Purified Water q.s. | 100 g |

The preservative was dissolved in approximately 50 g of warm purified water and after cooling to about 25°–30° the compound of formula (I) was added. In a separate container the emulsifying wax, mineral oil and white petrolatum were mixed well and heated to approximately 70°–80° C. The aqueous solution containing the compound of formula (I) was added to the warm mixture of emulsifying wax, mineral oil and petrolatum with vigorous mixing while cooling to 25° C. Additional purified water was added with mixing to bring the total amount to 100.0 g.

| (K)-Topical Lotion | |
| --- | --- |
| Ingredient | Amount per 100.0 mL |
| Compound of Formula (I) | 50.0 g |
| Carbomer, N.F. | 0.15 g |
| Triethanolamine | 0.15 g |
| Preservative | 0.5 g |
| Propyleneglycol | 5.0 g |
| Purified Water q.s. | 100 g |

The preservative was dissolved in approximately 50 g of warm purified water and after this solution was cooled to 25°–30° C., the compound of formula (I) was added. The carbomer was mixed in next followed by triethanolamine and propyleneglycol. Purified water was added to bring the total amount to 100 g and the formulation was mixed well.

We claim:

1. A compound of the formula (I):

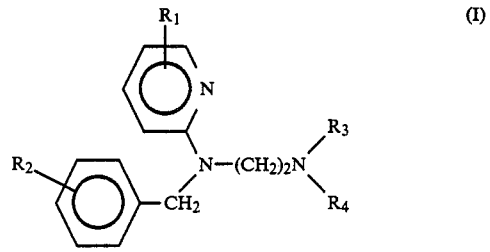

or a pharmaceutically acceptable salt thereof; wherein $R_1$ is —COOH, —CH=CH—COOH, —CH$_2$COOH, or (CH$_2$)$_2$COOH, $R_2$ is alkoxy (1–4 carbons), alkyl (1–4 carbons), hydrogen, or halogen, $R_3$ and $R_4$ may be the same or different and can be hydrogen, or lower alkyl (1-4 carbons) or $NR_3R_4$ is pyrrolidino.

2. A compound of claim 1 which is of the formula (Ia):

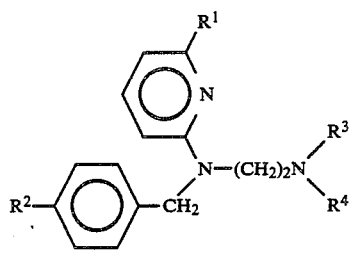

or a pharmaceutically acceptable salt thereof, wherein $R^1$-$R^4$ are as hereinbefore defined.

3. A compound of claim 1 which is of the formula (Ib):

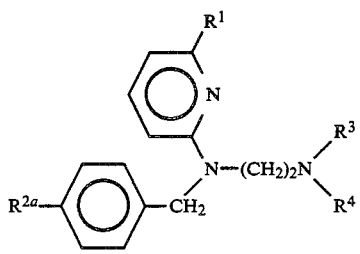

or a pharmaceutically acceptable salt thereof; wherein $R^{2a}$ is a $C_{1-4}$ alkyl or $C_{1-4}$ alkoxy group and $R^1$, $R^3$ and $R^4$ are as hereinbefore defined.

4. A compound of claim 1 which is of the formula (Ic):

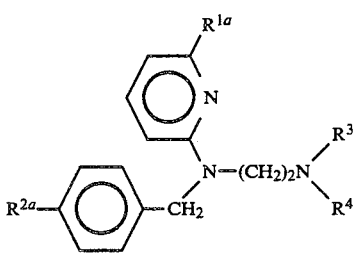

or a pharmaceutically acceptable salt thereof, wherein $R^{1a}$ is a group —$CO_2H$ or —$CH=CHCO_2H$, and $R^{2a}$, $R^3$ and $R^4$ are as hereinbefore defined.

5. A compound of claim 1 which is of the formula (Id):

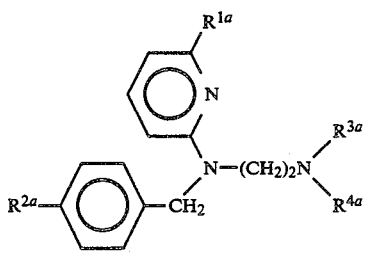

or a pharmaceutically acceptable salt thereof, wherein $R^{3a}$ and $R^{4a}$ are the same or different and each is a $C_{1-4}$ alkyl group; $R^{1a}$ and $R^{2a}$ are as hereinbefore defined.

6. A compound according to claim 5 wherein $R^{2a}$ is $C_{1-4}$ alkoxy.

7. A compound according to claim 5 wherein $R^3$ and $R^4$ are each methyl.

8. A compound according to claim 5 wherein $R^{2a}$ is methoxy.

9. A compound according to claim 7 wherein $R^{2a}$ is methoxy.

10. (E)-3-(6-N-dimethylaminoethyl)-4-methoxy-benzylamino)-2-pyridyl)acrylic acid or a pharmaceutically acceptable salt thereof.

11. (6-(N-(2-dimethylaminoethyl)-4-methoxybenzylamino)nicotinic acid or a pharmaceutically acceptable salt thereof.

12. A pharmaceutically acceptable salt of the compound of claim 1.

13. The salt of claim 10 which is a pharmaceutically acceptable salt.

14. The salt of claim 11 which is a pharmaceutically acceptable salt.

15. A method of obtaining an antihistiminic effect in a mammal in need thereof comprising the administration of an effective antihistiminic amount of the compound of claim 1, 2, 3, 4, 5, 6, 7, 8, 9, 10 or 11 to said mammal.

* * * * *